US011265391B1

(12) United States Patent
Baruch et al.

(10) Patent No.: US 11,265,391 B1
(45) Date of Patent: Mar. 1, 2022

(54) MEDICAL SERVICE PROVIDER RAPID RESPONSE SYSTEM

(71) Applicant: MedText Communications, LLC, Teaneck, NJ (US)

(72) Inventors: Howard Baruch, Englewood, NJ (US); Jacob Kustanowitz, Boca Raton, FL (US)

(73) Assignee: MEDTEXT COMMUNICATIONS, LLC, Teaneck, NJ (US)

( * ) Notice: Subject to any disclaimer, the term of this patent is extended or adjusted under 35 U.S.C. 154(b) by 864 days.

(21) Appl. No.: 15/628,052

(22) Filed: Jun. 20, 2017

Related U.S. Application Data

(60) Provisional application No. 62/352,586, filed on Jun. 21, 2016.

(51) Int. Cl.
*G16H 10/60* (2018.01)
*G06F 21/62* (2013.01)
(Continued)

(52) U.S. Cl.
CPC ............ *H04L 67/24* (2013.01); *G06F 19/328* (2013.01); *G06F 21/6245* (2013.01);
(Continued)

(58) Field of Classification Search
CPC ... G06F 19/328; G06F 21/6245; G06Q 40/08; G06Q 50/24; H04L 67/24; H04L 67/12; G16H 10/60
See application file for complete search history.

(56) References Cited

U.S. PATENT DOCUMENTS 6,302,844 B1 * 10/2001 Walker ................. A61B 5/1112
600/300
6,804,558 B2 * 10/2004 Haller ................ A61N 1/37264
607/30
(Continued)

FOREIGN PATENT DOCUMENTS

WO WO-2011028261 A2 * 3/2011 ......... G06F 19/3418

OTHER PUBLICATIONS

"Choosing the Medical Alert System that's Right for you!", LifeCall Medical Aled, Jan. 24, 2014, http://lifecall.com/choosing-the-medical-alert-system-thats-right-for-you/.
(Continued)

*Primary Examiner* — Rachel L. Porter
*Assistant Examiner* — Steven G Sanghera
(74) *Attorney, Agent, or Firm* — Fox Rothschild LLP

(57) ABSTRACT

A patient uses a token with multiple actuators to request assistance from a healthcare provider. When the patient activates one of the token's actuators, a nearby mobile device receives a signal from the relevant actuator, selects a code depending on which actuator was activated, and sends the code along with location data and a patient identifier to a server. The server uses the identifier to access a patient record for the patient and retrieve insurance data. The server will use the code, the location data and the insurance data to select an appropriate healthcare provider for the patient. The system will transmit a communication to the selected healthcare provider with a phone number for the patient's mobile device so that the healthcare provider can contact the patient.

20 Claims, 5 Drawing Sheets

(51) Int. Cl.
  *G06Q 40/08* (2012.01)
  *H04L 29/08* (2006.01)
  *H04L 67/54* (2022.01)
  *G06Q 50/24* (2012.01)
  *H04L 67/12* (2022.01)
  *G06F 19/00* (2018.01)

(52) U.S. Cl.
  CPC ............ *G06Q 40/08* (2013.01); *G06Q 50/24* (2013.01); *G16H 10/60* (2018.01); *H04L 67/12* (2013.01)

(56) References Cited

U.S. PATENT DOCUMENTS

| | | | | |
|---|---|---|---|---|
| 7,308,246 B2 * | 12/2007 | Yamazaki | ............ | G08B 25/016 379/56.3 |
| 7,639,137 B2 * | 12/2009 | Mukherjee | ......... | G06K 19/0672 340/10.1 |
| 8,458,097 B2 * | 6/2013 | Kenedy | .............. | G06Q 20/3674 705/51 |
| 8,533,475 B2 * | 9/2013 | Frikart | ................ | G06F 19/3418 713/171 |
| 9,491,277 B2 | 11/2016 | Vincent | | |
| 2006/0293570 A1 | 12/2006 | Croghan et al. | | |
| 2014/0136233 A1 | 5/2014 | Atkinson et al. | | |
| 2014/0273912 A1 | 9/2014 | Peh et al. | | |
| 2014/0278449 A1 * | 9/2014 | Kharraz Tavakol | .. | G06F 19/328 705/2 |

OTHER PUBLICATIONS

"What to look for in a medical aleri system", Consumer Reports, Jul. 2015, http://www.consumerreports.org/content/cro/en/health/news-archive/z2014/June/shouldYouBuyAMedicalAlertSystems.print.html.

* cited by examiner

MEDICAL SERVICE PROVIDER RAPID RESPONSE SYSTEM

RELATED APPLICATIONS AND CLAIM OF PRIORITY

This patent document claims priority to U.S. Provisional Patent Application No. 62/352,586, filed Jun. 21, 2016, the disclosure of which is fully incorporated into this filing by reference.

BACKGROUND

Rapid response systems for healthcare have existed for many years. Ranging from simple systems like the well-known "LifeCall" system of the late 1980's to current sophisticated smartphones, patients have had a variety of ways to quickly connect with healthcare providers and emergency responders. However, when providing an emergency response, the prior systems are not able to automatically assess important characteristics of the patient that would be useful to select the proper response team or protocol. Instead, the patient must provide detailed information that a call center operator will use to manually connect the patient with the appropriate provider, or the patient must actively select and directly contact his or her appropriate provider.

This document describes novel methods and systems that address the problems described above, as well as additional issues.

SUMMARY

In various embodiments, a patient uses a token with multiple actuators to request a healthcare provider. When the patient activates an actuator on the token, the patient's electronic device receives a signal from the relevant actuator, selects a code depending on which actuator was activated, and sends the code along with location data and a patient identifier to a remote server. The server uses the identifier to access a patient record for the patient and retrieve insurance data. The server will use the code, the location data and the insurance data to select an appropriate healthcare provider for the patient. The system will transmit a communication to the selected healthcare provider with a phone number for the patient's electronic device so that the healthcare provider can contact the patient.

In various embodiments, a system for implementing a healthcare provider response for a patient includes a token that includes two or more actuators and a transmitter, an electronic device and a remote server. When a person activates one of the actuators on the token, the token generates and transmits a signal that corresponds to the actuator. When the electronic device receives the signal from a token, it will identify which of the actuators was selected and initiated the signal, determine a location of the token, retrieve a patient identifier, and transmit a healthcare service request to the server. The healthcare service request will include the location, the patient identifier, and a code that is associated with the selected actuator. The server will receive the healthcare service request from the electronic device, and it will access a patient database and using the patient identifier to identify a patient profile in the patient database. The patient profile will include insurance data. The server will use the insurance data and the code to select a healthcare provider, and it will automatically send a communication to the selected healthcare provider. The communication will include a name of the patient, the location, and an identifying code for the electronic device that the selected healthcare provider can use to contact the patient via the electronic device.

Optionally, the electronic device may generate the code as a code corresponding to a healthcare provider type with which the selected actuator is associated.

Optionally, when the server uses the insurance data and the code to select a healthcare provider, it may do so in response to detecting that the healthcare provider type associated with the code is a primary care provider or a specialist. If so, the selection of the provider may include identifying a primary care provider or specialist that is associated with the patient profile and determining whether the location corresponds to a geographic region of the identified primary care provider. If the location corresponds to the geographic region of the identified primary care provider, the server may select the identified primary care provider or specialist as the selected healthcare provider. If the location does not correspond to the geographic region of the identified primary care provider or specialist, the server may select as the selected healthcare provider an alternate primary care provider or specialist who is in a region to which the location corresponds, and who is a participating provider with an insurance plan that corresponds to the insurance data.

Optionally, when the server uses the insurance data and the code to select a healthcare provider, it may identify a healthcare provider who is: (i) a healthcare provider of the healthcare provider type that is associated with the code; (ii) in a region to which the location data corresponds; and (iii) a participating provider with an insurance plan that corresponds to the insurance data.

Optionally, when the electronic device identifies which of the actuators was selected and initiated the signal, the electronic device may access a structured knowledge base of known signal characteristics and actuator identifiers and extract, from the knowledge base, the actuator identifier of the actuator that is associated with signal characteristics matching those of the signal.

The patient identifier may be included in the signal, or the electronic device may look up the patient identifier from a data set in which patient identifiers are associated with signal characteristics and retrieve the patient identifier that corresponds to the signal. In addition, in some embodiments the electronic device may receive biometric data for the patient from a wearable electronic device and it may include the biometric data in the healthcare service request that it sends to the server. The server may in turn send the biometric data to the selected healthcare provider.

Optionally, the signal may be an analog signal, and the step of identifying which of the actuators was selected and initiated the signal may include identifying a frequency of the signal and determining which of the actuators is associated with the frequency. Alternatively, the signal may include a set of data packets, and the step of identifying which of the actuators was selected and initiated the signal comprises identifying a code in the data packets and determine which of the actuators is associated with the code in the data packets. Alternatively or in addition, if the signal includes a sequence of pulses, the step of identifying which of the actuators was selected and initiated the signal may include determining which of the actuators is associated with the sequence of pulses.

DETAILED DESCRIPTION

Figure 1:
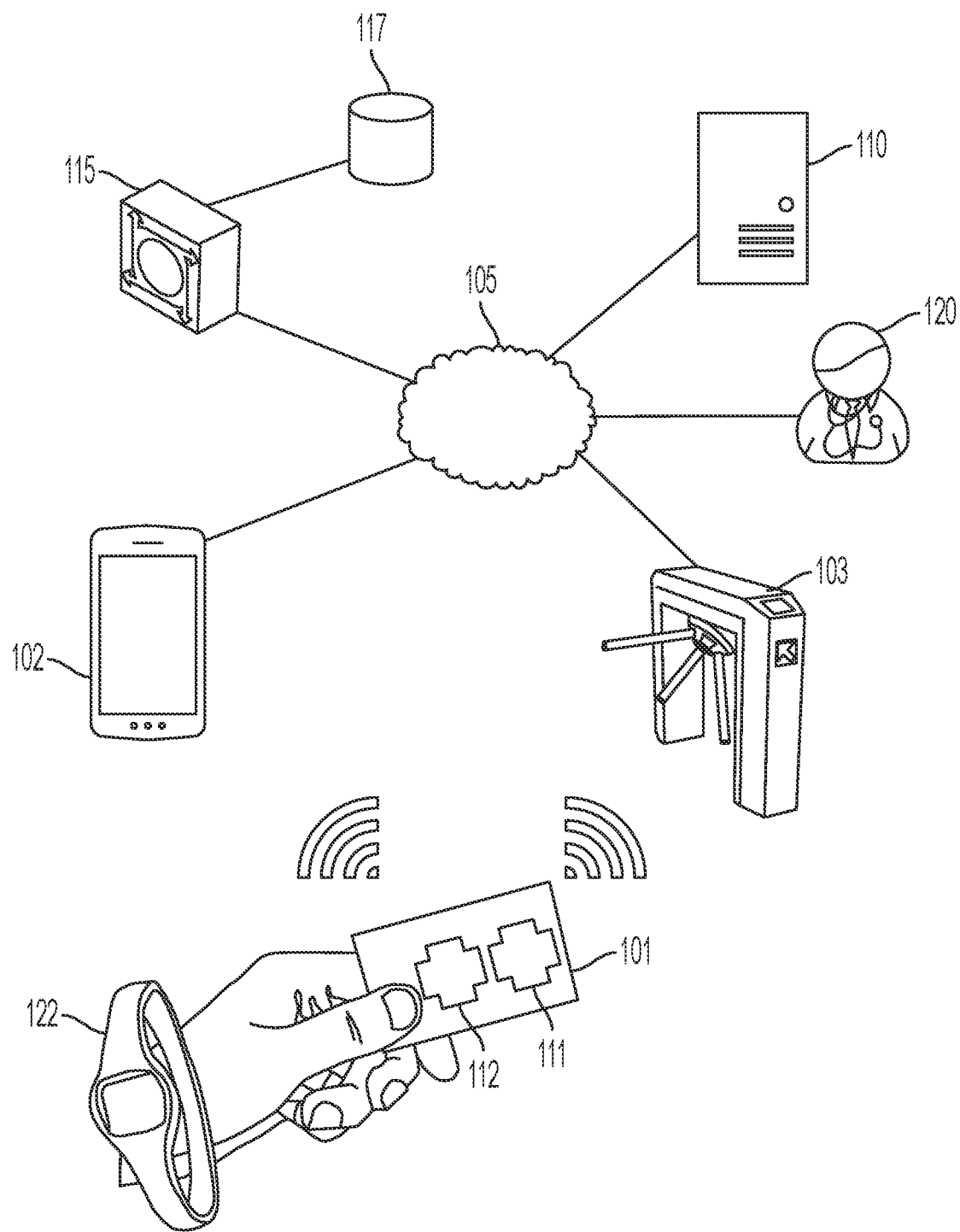
FIG. 1 illustrates various elements of an example of a system for implementing healthcare provider response to a patient.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to." All patents referred to in this document are fully incorporated by reference.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

In this document, the terms "electronic device" and "server" each refer to an electronic device or a system of networked devices having a processor and memory. The memory may contain programming instructions in the form of a software application that, when executed by the processor, causes the device to perform one or more processing operations according to the programming instructions. An electronic device will also include one or more communication hardware components such as a transmitter and/or receiver that will enable the device to send and/or receive signals to and/or from other devices, whether via a communications network or via near-field or short-range communication protocols. Examples of electronic devices include personal computers, servers, mainframes, virtual machines, containers, gaming systems, televisions, digital home assistants and mobile electronic devices such as smartphones, fitness tracking devices, wearable virtual reality devices, Internet-connected wearables such as smart watches and smart eyewear, personal digital assistants, cameras, tablet computers, laptop computers and media players. Electronic devices also may include appliances and other devices that can communicate in an Internet-of-things arrangement, such as smart thermostats, refrigerators, connected light bulbs and other devices. Electronic devices also may include components of vehicles such as dashboard entertainment and navigation systems, as well as on-board vehicle diagnostic and operation systems. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. In various embodiments, an electronic device may be associated with a phone number and a media access control (MAC) address.

In this document, the terms "processor" and "processing device" refers to one or more hardware components of an electronic device that execute(s) programming instructions. The terms encompass both a single processor embodiment, as well as an embodiment with multiple processors that together implement various steps of a process. Unless the context specifically states that a single processor is required or that multiple processors are required, the terms "processor" and "processing device" include both the singular and plural embodiments.

FIG. 1 illustrates various elements of an example of a system for implementing healthcare provider response to a patient. The system includes a token 101 having two or more token actuators 111, 112. The token is a device having components that can generate a signal and communicate that signal to a mobile electronic device 102 or a stationary electronic device 103 (such as a turnstile or other building admission system as shown) having a token reader so that the electronic device can serve as a reading device. Examples of tokens including smart cards, wearable safety devices such as medical alarm bracelets and pendants, and other items. Examples of tokens include medical asset tracking tags that include wireless call buttons, and smart cards with integral switches such as those disclosed in U.S. Pat. Nos. 6,050,494; 7,900,843; and 8,322,624, the disclosures of which are fully incorporated into this document by reference. Although in some embodiments a token may include multiple actuators in a common housing, in other embodiments a token may house each actuator in a separate housing in which case the "token" may include multiple devices. The token readers of the external reading devices 102, 103 will include signal detection equipment such as an antenna or other card reading device that can detect the signal generated by the token. The token reader's electronic device and the token may be paired with each other, such as through a secure login process or electronic handshaking process, so that only a paired electronic device can accept and process signals from token to perform the functions described below, rather than any nearby electronic device.

Each actuator 111, 112 includes a switch that generates a signal when the switch is activated. The switch may be a pressure-sensitive switch such as a miniature snap-action switch or micro switch. Alternatively or in addition, the switch may be a capacitance touch switch or resistance touch switch that activates when touched by a human finger or other body part. Other types of switches such as piezo touch switches may be used as well. In this embodiment, the actuators may be included in a pocket-sized or wallet-sized card.

Each actuator also includes or is connected to a transmitter such as a Bluetooth, radio frequency identification (RFID), or other antenna or transmitter capable of near field communication.

Each actuator generates a unique signal in that no two actuators of the token will generate the same signal. If the transmitter is an analog transmitter, then a difference between the signals may be a difference in frequency of the signal, or a difference in pattern (such as a sequence of pulses of varying durations). If the transmitter is a digital transmitter, then a difference between the signals may be that each signal is a data packet containing a unique code, or a difference in pattern (such as may be achieved through pulse width modulation). Thus, each actuator may correspond to a different message, condition, or situation. For example, one actuator may signal that the patient needs to contact his or her primary care physician. A second actuator may signal that the patient needs to contact an emergency responder such as an emergency medical service (EMS). A third actuator may signal that the patient needs to contact a particular medical specialist, such as a provider who is experienced in a particular condition that the patient has such as diabetes or lupus. Thus, the system may determine a category of healthcare provider to respond to the patient's call depending on which actuator was actuated.

When an actuator is activated, a processor of the system can implement program instructions to access a structured knowledge base (such as a database stored in one or more memory devices) of known signal characteristics and actuator identifiers and use that knowledge base to identify and extract an identification of the actuator that corresponds to the detected signal type. The processor may be in the token 101 itself, in which case the processor will cause the token to generate and send a signal that uniquely identifies which of the token's actuators was activated. Alternatively, the processor may be in the external reading device 102 or 103, in which case the external reading device will receive the token's signal via a communication component such as a near field receiver, and the device may access the data store to identify which actuator has been associated with a signal having characteristics of the detected signal. The data store may be located in the external reading device (102 or 103), or it may be located in a remote data storage facility 110 which the electronic device may access via one or more communication networks 105.

The processor of the external reading device 102 or 103 may obtain a location of the device, such as from a memory (if the device is stationary) or via a global positioning system (GPS) receiver of the device if the device is mobile. The external reading device also may retrieve a patient identifier, either from a memory of the device (if the device is dedicated to the patient), or from data contained in a signal of the token. The patient identifier may be in the token's signal, or the token's signal may include another identifier that the reading device may use to query the data store 110 for a patient identifier that corresponds to the token identifier.

The reading device may use the detected signal to determine a code that is associated with the actuator that was activated. The reading device may transmit the code, the location, and the patient identifier to transmit a healthcare service request to a remote healthcare dispatching system server 115 via the communication network 105.

The dispatching system server 115 will access a database 117 and use the patient identifier to locate a patient profile for the patient who initiated the signal, along with insurance data for the patient. The same database 117 or a different database also may include data identifying which healthcare providers correspond to the patient's insurance data (such as by being in network), and of those providers which of them are proximate to the patient's location (such as being within a threshold distance from the patient, or being closer to the patient than any other qualifying provider). The dispatching system server 117 will select a healthcare provider that both corresponds to the patient's insurance data (i.e., is a participating provider in the patient's insurance plan) and that is proximate to the patient's location. The dispatching system server may then transmit a communication to a healthcare provider communication device 120 so that the provider receives the patient's name, location, an identification code (such as a phone number) that can be used to initiate a communication with the electronic device, condition information, and/or other information that the provider can use to respond to the patient's signal.

Optionally, system may include a wearable electronic device that is configured to collect biometric data from the patient, such as a fitness tracker, an accelerometer that can detect patient movements (such as sudden downward movements that may be associated with a fall), a skin temperature sensor, a pulse rate monitor and/or a heart rate monitor. The biometric data collection device 122 may be worn or held by the patient and it may be paired with the token 101 and/or the reading device 102 to collect and transfer the measured biometric data to the healthcare provider device 120 via the external reading device 102.

Figure 2:
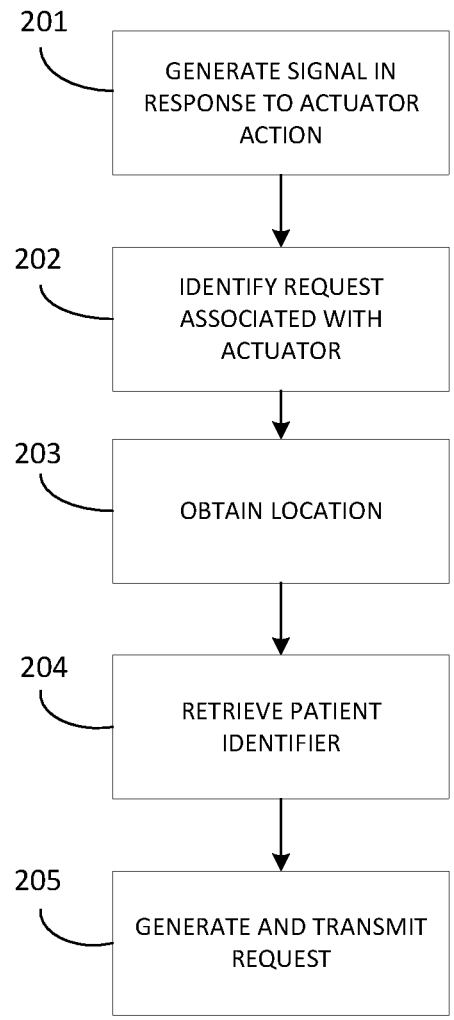
FIG. 2 is s flowchart illustrating an example process flow that patient-facing components of the system may implement.

FIG. 2 is a flow diagram illustrating example methods of operation of certain components of the system that will be worn by or proximate to the patient. When the patient actuates one of the actuators on the actuators on the token, the actuator will generate a signal 201 that a processor of the token or a proximate mobile device may use to identify a request 202 that corresponds to one or more characteristics of the signal. For example, the signal may use a code and the processor may access a data set of requests and corresponding codes to select the request that corresponds to the code. The system will also obtain a location of the proximate mobile device 203, retrieve a patient identifier 204 either from the mobile device or by using data received from the token, and transmit a healthcare service request to a remote server 205. The healthcare service request will include the location, the patient identifier, a phone number for the patient's mobile device, and the request (i.e., a code that is associated with the selected actuator). If the patient is wearing a biometric sensor such as that discussed above in the context of FIG. 1, then they request also may include biometric data captured by the sensor.

Figure 3:
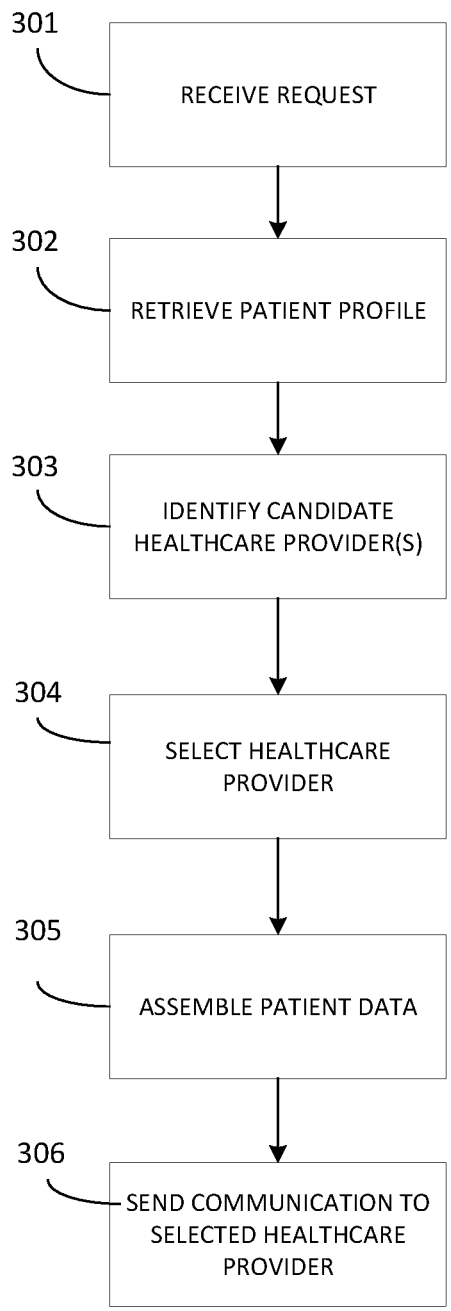
FIG. 3 flowchart illustrating an example process flow that a dispatching server of the system may implement.

FIG. 3 illustrates various actions that the remote server may initiate when it receives the request 301. The server will use the patient identifier to locate a patient profile 302 from a patient database by selecting the profile that includes the patient identifier. The patient profile also will include insurance data for the patient, such as a policy number, insurance provider identifier, and/or identifying information for one or more healthcare providers that participate in the patient's insurance program. Alternatively, identifying data for healthcare providers may be maintained in a separate database along with data indicating the insurance plans with which each healthcare provider participates.

In either scenario, the system may use the insurance data to identify one or more healthcare providers 303 to respond to the patient's request. The system may use one or more rules to identify the candidate healthcare providers and then select 304 which of them will be invited to respond to the request. For example, the rules may require that each identified healthcare provider: (i) participate in the patient's insurance program; (ii) have profile data that corresponds to the category of the patient's request (e.g., primary care physician specialist, EMS, or other type of provider; and (iii) have geographic data indicating that they are proximate to the GPS location of the patient's electronic device (such as by being within a threshold distance from the patient, or being one of the X most closest providers to the patient's location). If the system identifies multiple candidate providers, it may select one of the providers using any suitable algorithm that ranks and scores the candidate healthcare providers. For example, the system may identify the GPS location of the patient's electronic device and select the healthcare provider that is closest to the GPS location. The system also may access provider profile data for each candidate provider, and/or a profile of the patient's primary care physician, and select one of the candidate providers who the patient's primary care physician has selected as a preferred provider (as indicated in either or both of the primary physician's profile or the candidate provider's profile). If the provider profile data includes subjective measurements such as a responsiveness score, the system may select the candidate provider having the highest responsiveness score. Optionally, the system may use an algorithm that is a function of any or all of these parameters, optionally with additional parameters, optionally with one or more of the parameters adjusted by a weighting factor to give it more or less influence on the selection than other factors.

The system will then automatically send a communication to the selected healthcare provider 306. The communication may include a name of the patient, the location, and a phone number for the mobile electronic device. If the request included biometric data, then the system also may assemble some or all of this data 305 and include it in the communication to the selected healthcare provider, For example, if the system detects that the patient has selected an actuator that corresponds to a primary care provider, the system may identify a primary care provider that is associated with the patient profile, and it may determine whether the GPS data corresponds to a geographic region of the identified primary care provider. If the GPS data corresponds to the geographic region of the identified primary care provider, the system will select the identified primary care provider as the selected healthcare provider. If the GPS data does not correspond to the geographic region of the identified primary care provider, the system will select an alternate primary care provider who is in a region to which the GPS data corresponds, and who is a participating provider with an insurance plan that corresponds to the insurance data.

As another example, if the system detects that the patient has selected an actuator that corresponds to a particular type of specialist, the system may identify a specialist of that type who is associated with the patient profile, and it may determine whether the GPS data corresponds to a geographic region of the identified specialist. If the GPS data corresponds to the geographic region of the identified specialist, the system will select the identified specialist as the selected healthcare provider. If the GPS data does not correspond to the geographic region of the identified primary care provider, the system will select an alternate specialist in the category who is in a region to which the GPS data corresponds, and who is a participating provider with an insurance plan that corresponds to the insurance data.

Figure 4:
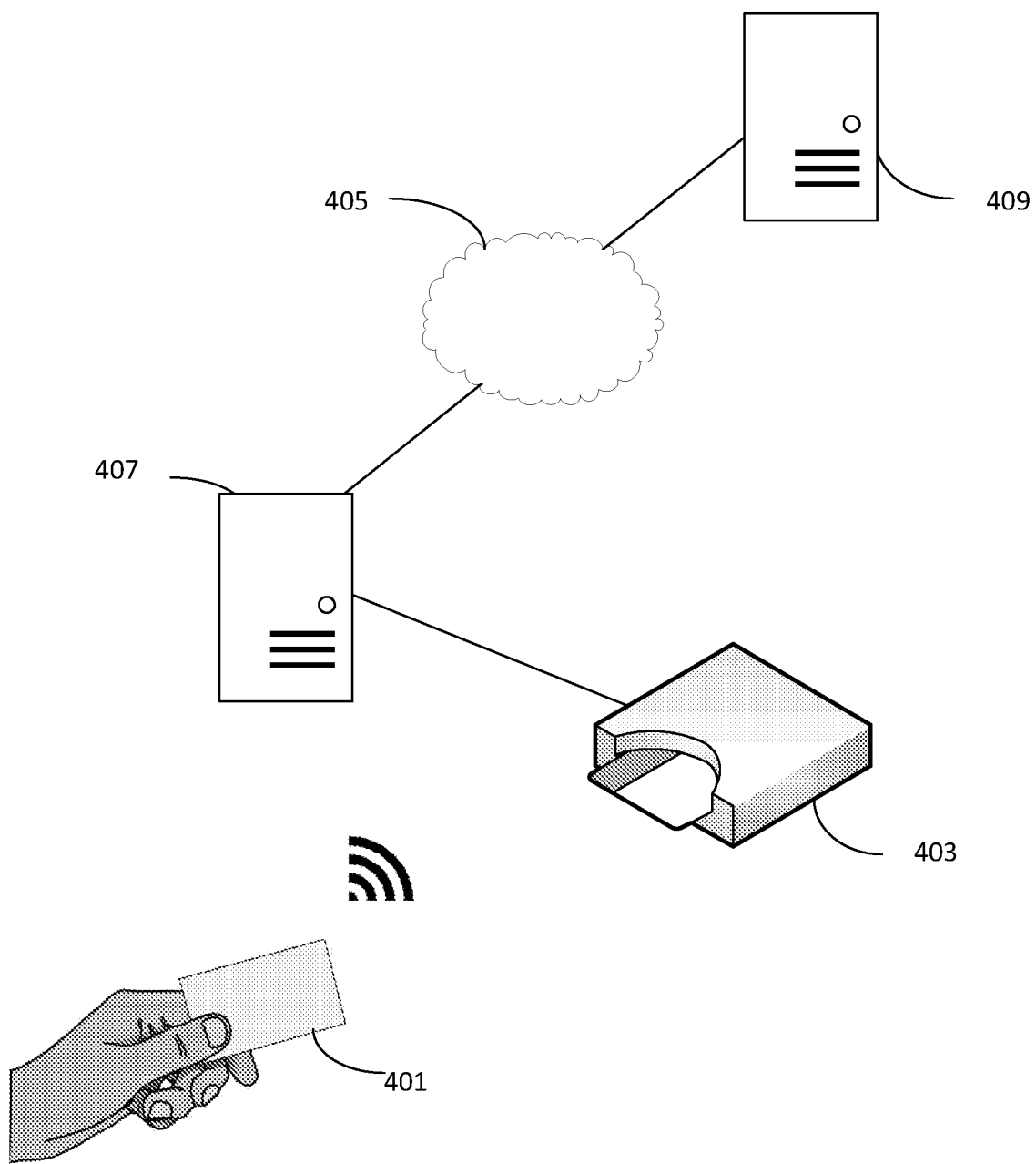
FIG. 4 illustrates elements of an optional additional application of a system for implementing healthcare provider response to a patient.

In another embodiment, a patient may select an actuator of the token to check in at a particular healthcare provider facility. For example, referring to FIG. 4, a healthcare facility such as a medical practice office, a hospital or clinic, a pharmacy, a medical laboratory, includes a token reading device 403 that includes a receiver that can detect a signal of the token. When a user (such as a patient) enters the facility with a token 401 and is within range of the token reading device 403, the user may activate an actuator of the token 401 and transmit an ID code to the token. The ID code may be associated with the user, the token, or both.

The system may include a local server 407 that is in wired or wireless communication with the token reading device 403, and a remote server 409 that includes or has access to a data store of electronic medical records for various patients. Each patient record includes personal identification information for the patient to whom the record applies (such as name or insurance policy number, and the identification code).

The remote server 409 may receive information from the token reading device 403 and local server 405 of the healthcare facility via a communication network 405 such as the Internet. Alternatively, the remote server 409 and its data store may be integral with the local computing device 407, or it may be connected to the local computing device 407 on the healthcare facility's local network. In either way, the server 409 and its data store may also communicate with one or more additional healthcare facilities so that additional facilities may retrieve the patient's information when the patient activates his or her token in those facilities in the future.

If, upon entry into a facility, the data store contains a patient record that contains the token or patient ID, the server will determine that the patient of that record has entered the network, and it may automatically generate a patient intake record for that patient. The patient intake record may include information such as a current date, time, and personal identification for the patient. If the data store does not have a token or patient ID, the system may prompt or wait for a local administrator to create a new patient record for the patient, or to associate an existing patient record with the known ID.

Thus, the devices and processes described above can be implemented in applications such as a token that also is a patient identification card for a medical network, an insurance plan, or a healthcare savings account. In applications such as these, the card/token will also include data indicating a network with which the cardholder participates (such as an insurance plan or a healthcare system account). The system may then use this data or associated data from the patient's profile—such as an insurance plan identifier or a healthcare system identifier—to select a healthcare provider and ensure that the provider is approved by or otherwise affiliated with the insurance plan or healthcare system.

Figure 5:
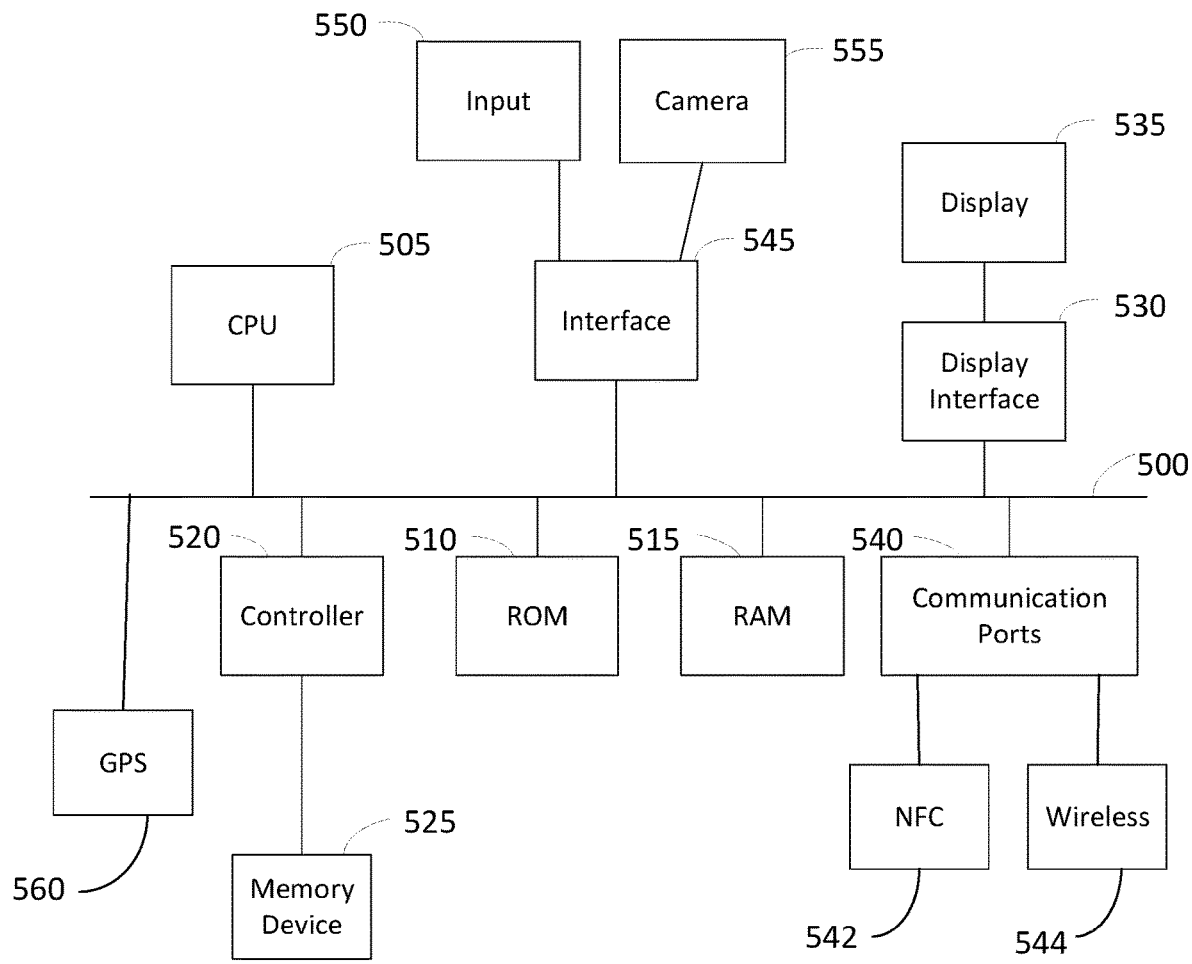
FIG. 5 depicts an example of internal hardware that may be included in any of the electronic components of the system.

FIG. 5 depicts an example of internal hardware that may be included in any of the electronic components of the system, such as the user's smartphone or a local or remote computing device in the system. An electrical bus 500 serves as an information highway interconnecting the other illustrated components of the hardware. Processor 505 is a central processing device of the system, configured to perform calculations and logic operations required to execute programming instructions. As used in this document and in the claims, the terms "processor" and "processing device" may refer to a single processor or any number of processors in a set of processors, whether a central processing unit (CPU) or a graphics processing unit (GPU) or a combination of the two. Read only memory (ROM), random access memory (RAM), flash memory, hard drives and other devices capable of storing electronic data constitute examples of memory devices 525. A memory device may include a single device or a collection of devices across which data and/or instructions are stored.

An optional display interface 530 may permit information from the bus 540 to be displayed on a display device 535 in visual, graphic or alphanumeric format. An audio interface and audio output (such as a speaker) also may be provided. Communication with external devices may occur using various communication devices such as a wireless antenna 544, an RFID tag and/or short-range or near-field communication transceiver 542, each of which may optionally communicatively connect with other components of the device via one or more communication ports 540. A communication device 540 may be attached to a communications network, such as the Internet, a local area network or a cellular telephone data network.

The hardware may also include a user interface sensor 545 that allows for receipt of data from input devices 550 such as a keyboard, a mouse, a joystick, a touchscreen, a touch pad, a remote control, a pointing device and/or microphone. Digital image frames also may be received from a camera 555 that can capture video and/or still images. The system also may include a position sensor that serves as a location tracking component such as a global positioning system (GPS) receiver 560 that can receive data from an external system to enable the device to identify its current location. A position sensor also may include a network detection sensor that can identify a local network to which the electronic device is communicatively connected.

The above-disclosed features and functions, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A system for implementing a healthcare provider response for a patient, the system comprising:
    a token that includes a plurality of actuators and a transmitter;
    an electronic device that includes:
        a processing device,
        a receiver for receiving a signal from the token in response to selection of one of the actuators; and
        programming instructions that are configured to cause the processing device to process the signal and identify which of the actuators was selected and initiated the signal,
        a communications component that is in communication with a server,
        a position sensor, and
        additional programming instructions that are configured to cause the processing device to implement an alert function which, upon identifying which of the actuators was been selected:
            obtain location data from the position sensor,
            retrieve a patient identifier, and
            transmit a healthcare service request to a server, wherein the healthcare service request comprises the location, the patient identifier, and a code that is associated with the selected actuator; and
    the server, wherein the server includes programming instructions that are configured to cause the server to:
        receive the healthcare service request from the electronic device,
        access a patient database and use the patient identifier to identify a patient profile in the patient database, wherein the patient profile comprises insurance data,
        automatically use the insurance data and the code to select a healthcare provider within an insurance network, and
        automatically send a communication to the selected healthcare provider, wherein the communication includes a name of the patient, the location data, and an identification code for the electronic device that the selected healthcare provider can use to contact the patient via the electronic device.

2. The system of claim 1, wherein:
    the electronic device is a mobile electronic device;
    each actuator of the token comprises a switch;
    each actuator of the token is configured to, when selected, generate a signal of a type that the mobile electronic device can differentiate from the signals of each other actuator of the token; and
    the mobile electronic device also comprises programming instructions that are configured to generate the code as a code corresponding to a healthcare provider type with which the selected actuator is associated.

3. The system of claim 2, wherein the programming instructions of the server that are configured to cause the server to use the insurance data and the code to select a healthcare provider comprise instructions to, in response to detecting that the healthcare provider type associated with the code is a primary care provider:
    identify a primary care provider that is associated with the patient profile;
    determine whether the location data corresponds to a geographic region of the identified primary care provider;
    if the location data corresponds to the geographic region of the identified primary care provider, select the identified primary care provider as the selected healthcare provider; and
    if the location data does not correspond to the geographic region of the identified primary care provider, select as the selected healthcare provider an alternate primary care provider who:
        is in a region to which the location data corresponds, and
        is a participating provider with an insurance plan that corresponds to the insurance data.

4. The system of claim 2, wherein the programming instructions of the server healthcare provider are configured to cause the server to use the insurance data and the code to select a healthcare provider comprise instructions to, in response to detecting that the healthcare provider type associated with the code is a specialist:
    identify a specialist that is associated with the patient profile and the signal;
    determine whether the location data corresponds to a geographic region of the identified specialist;
    if the location data corresponds to the geographic region of the identified primary care provider, select the identified specialist as the selected healthcare provider; and
    if the location data does not correspond to the geographic region of the identified specialist, select as the selected healthcare provider an alternate specialist who:
        is in a region to which the location data corresponds, and
        is a participating provider with an insurance plan that corresponds to the insurance data.

5. The system of claim 2, wherein the programming instructions of the server that are configured to cause the server to use the insurance data and the code to select a healthcare provider comprise instructions to identify a healthcare provider who:
    is a healthcare provider of the healthcare provider type that is associated with the code;
    is in a region to which the location data corresponds; and is a participating provider with an insurance plan that corresponds to the insurance data.

6. The system of claim 1, wherein the programming instructions of the electronic device that are configured to cause the processing device to identify which of the actuators was selected and initiated the signal comprise instructions to:
access a structured knowledge base of known signal characteristics and actuator identifiers; and
extract, from the knowledge base, the actuator identifier of the actuator that is associated with signal characteristics matching those of the signal.

7. The system of claim 1, wherein:
the patient identifier is included in the signal; and
the electronic device also includes programming instructions to:
receive biometric data for the patient from a wearable electronic device, and
include the biometric data in the healthcare service request.

8. The system of claim 1, wherein:
the signal is an analog signal; and
the programming instructions that are configured to cause the processing device to process the signal and identify which of the actuators was selected and initiated the signal comprises instructions to identify a frequency of the signal and determine which of the actuators is associated with the frequency.

9. The system of claim 1, wherein:
the signal comprises a set of data packets; and
the programming instructions that are configured to cause the processing device to process the signal and identify which of the actuators was selected and initiated the signal comprises instructions to identify a code in the data packets and determine which of the actuators is associated with the code in the data packets.

10. The system of claim 1, wherein:
the signal comprises a sequence of pulses; and
the programming instructions that are configured to cause the processing device to process the signal and identify which of the actuators was selected and initiated the signal comprises instructions to determine which of the actuators is associated with the sequence of pulses.

11. A method of implementing a healthcare provider response for a patient, the method comprising:
by an electronic device that includes a processing device and a receiver:
receiving a signal from a token that includes a plurality of actuators, wherein the token generated and transmitted the signal in response to selection of one of the actuators;
identifying which of the actuators was selected and initiated the signal,
determining a location of the token,
retrieving a patient identifier, and
transmitting a healthcare service request to a server, wherein the healthcare service request comprises the location, the patient identifier, and a code that is associated with the selected actuator; and
by the server:
receiving the healthcare service request from the electronic device,
accessing a patient database and using the patient identifier to identify a patient profile in the patient database, wherein the patient profile comprises insurance data,
using the insurance data and the code to automatically select a healthcare provider within an insurance network, and
automatically sending a communication to the selected healthcare provider, wherein the communication includes a name of the patient, the location, and an identification code for the electronic device that the selected healthcare provider can use to contact the patient via the electronic device.

12. The method of claim 11 further comprising, by the electronic device, generating the code as a code corresponding to a healthcare provider type with which the selected actuator is associated.

13. The method of claim 12, wherein when the step of, by the server, using the insurance data and the code to select a healthcare provider comprises, in response to detecting that the healthcare provider type associated with the code is a primary care provider:
identifying a primary care provider that is associated with the patient profile;
determining whether the location corresponds to a geographic region of the identified primary care provider;
if the location corresponds to the geographic region of the identified primary care provider, selecting the identified primary care provider as the selected healthcare provider; and
if the location does not correspond to the geographic region of the identified primary care provider, selecting as the selected healthcare provider an alternate primary care provider who is:
in a region to which the location corresponds, and
is a participating provider with an insurance plan that corresponds to the insurance data.

14. The method of claim 12, wherein the step of, by the server, using the insurance data and the code to select a healthcare provider comprises, in response to detecting that the healthcare provider type associated with the code is a specialist:
identifying a specialist that is associated with the patient profile and the signal;
determining whether the location corresponds to a geographic region of the identified specialist;
if the location corresponds to the geographic region of the identified primary care provider, selecting the identified specialist as the selected healthcare provider; and
if the location does not correspond to the geographic region of the identified specialist, selecting as the selected healthcare provider an alternate specialist who:
is in a region to which the location corresponds, and
is a participating provider with an insurance plan that corresponds to the insurance data.

15. The method of claim 12, wherein the programming instructions of the server that are configured to cause the server to use the insurance data and the code to select a healthcare provider comprise instructions to identify a healthcare provider who:
is a healthcare provider of the healthcare provider type that is associated with the code;
is in a region to which the location data corresponds; and
is a participating provider with an insurance plan that corresponds to the insurance data.

16. The method of claim 11, wherein the step of, by the electronic device, identifying which of the actuators was selected and initiated the signal comprises:
accessing a structured knowledge base of known signal characteristics and actuator identifiers; and extracting, from the knowledge base, the actuator identifier of the actuator that is associated with signal characteristics matching those of the signal.

17. The method of claim 11, wherein:
the patient identifier is included in the signal; and
the method also includes, by the electronic device,
receiving biometric data for the patient from a wearable electronic device, and
including the biometric data in the healthcare service request.

18. The system of claim 11, wherein:
the signal is an analog signal; and
the step of identifying which of the actuators was selected and initiated the signal comprises identifying a frequency of the signal and determining which of the actuators is associated with the frequency.

19. The method of claim 11, wherein:
the signal comprises a set of data packets; and
the step of identifying which of the actuators was selected and initiated the signal comprises identifying a code in the data packets and determine which of the actuators is associated with the code in the data packets.

20. The method of claim 11, wherein:
the signal comprises a sequence of pulses; and
the step of identifying which of the actuators was selected and initiated the signal comprises determining which of the actuators is associated with the sequence of pulses.

* * * * *